US00PP16669P3

(12) United States Plant Patent
Fleming et al.

(10) Patent No.: US PP16,669 P3
(45) Date of Patent: Jun. 20, 2006

(54) ***HIBISCUS* PLANT NAMED: 'CHERUB'**

(50) Latin Name: ***Hibiscus moscheutos*×*H. rosa-sinensis***
Varietal Denomination: Cherub

(76) Inventors: David Whitman Fleming, deceased, late of Lincoln, NE (US); by Gretchen Zwetzig, legal representative, 8101 S. 14th St., Lincoln, NE (US) 68512

( * ) Notice: Subject to any disclaimer, the term of this patent is extended or adjusted under 35 U.S.C. 154(b) by 0 days.

(21) Appl. No.: 10/207,249

(22) Filed: Jul. 30, 2002

(65) Prior Publication Data

US 2004/0025214 P1 Feb. 5, 2004

(51) Int. Cl.
*A01H 5/00* (2006.01)

(52) U.S. Cl. ..... Plt./257
(58) Field of Classification Search ..... Plt./257
See application file for complete search history.

(56) References Cited

U.S. PATENT DOCUMENTS

PP13,751 P2 * 4/2003 Zwetzig et al. ..... Plt./257

OTHER PUBLICATIONS http://forums.gardenweb.com/forums/load/hibisc/msg0612-0228352.html.*
http://www.linders.com/products/annuals/annuals–article–t.html?id=8358&table=products.*
http://www.windmillgarden.com/garden_thymes/special-info_march.shtml.*

* cited by examiner

*Primary Examiner*—Kent Bell
*Assistant Examiner*—W. C. Haas

(57) ABSTRACT

A new and distinct cultivar of winter hardy *hibiscus* plant named 'Cherub' is the result of a unique hybridization. This new and distinct cultivar is characterized primarily as to novelty by its tropical aspects, its extreme cold hardiness to Zone 4, its medium-sized, thick-textured, tubular pink flowers with recurved petal edges and its shiny Maple-like green leaves and unusual pyramidal compactness of about 3 feet, its vigorous and uniform growth habit, and its floriferous nature from midsummer until frost, and its genetic achievement as a cross between a tropical and hardy *Hibiscus*.

1 Drawing Sheet

Botanical designation: *Hibiscus moscheutos*×*H. rosa-sinensis*.
Variety denomination: 'Cherub'.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined and noticeably shiny, Maple-like, green leaves which have smooth margins and pink buds which combined compliments the landscape;

(b) Medium-sized flowers that are outstanding for their soft pink overlapping petals with tubular shape having recurved petal edges;

(c) The plant being very floriferous with flowers that stay open at least one full day, sometimes two days, (d) The plant being small but vigorous with stouter stems, compact and "pyramidal" breaking action which gives it unique landscape utility; and (e) The plant being so hardy that it can consistently withstand winter temperatures of at least −30 degrees Fahrenheit.

(f) The plant being a genetic achievement as a hybrid between a tropical and hardy *Hibiscus*.

SUMMARY OF THE INVENTION

'Cherub' was the result of a 40-year breeding program. Its ancestry includes *Hibiscus moscheutos* and *Hibiscus rosa-sinensis*. More specifically, the plant resulted from multiple crossings with an unnamed proprietary *Hibiscus rosa-sinensis* (unpatented) and an unnamed proprietary *Hibiscus moscheutos* (unpatented). The single seedling which most nearly met all of the above named standards was selected.

This new plant first bloomed in the summer if 1990 and was selected by David Fleming and Gretchen Zwetzig on David Fleming's property in Lincoln, Nebr. Asexual propagation of the plant by cuttings and root division has shown that the unique and distinguishing features of the plant are faithfully transmitted from generation to generation and appear to be fixed.

Since its origin, the plant has bloomed from midsummer until frost, while exhibiting the aforementioned distinctive characteristics. This TROPICAL-HARDY™ *Hibiscus* plant greatly contributes to the market with its tropical aspect, shear beauty and utter refinement, its compact growth habit, its enhanced resistance to disease and insects, its stability through extremes in rain and drought, and its extreme hardiness.

BRIEF DESCRIPTION OF THE DRAWING

The flower and foliage of the cultivar are shown in the attached photographs. More specifically, the drawing a close-up of the flower and foliage. The plant in the photograph was apx. 5 years of age shown in Lincoln, Nebr.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with the *Dictionary of Color* (Maerz and Paul), while general color recitations are consistent with ordinary American color terminology.

'Cherub' has not been observed under all possible environment conditions. It is to be understood that the phenotype may vary significantly with variations in environment such as temperature, light intensity, and day length, without, however any difference in genotype of the plant. The following botanical characteristics and observations are gathered from a 5 year old plant when grown under normal outdoor conditions in Lincoln, Nebr. (USDA Plant Hardiness Zone 4).

THE PLANT

Parentage:

Seed parent: *Hibiscus moscheutos.* Unnamed and unpatented Fleming seedling.

Pollen parent: *Hibiscus rosa-sinensis.* Unnamed and unpatented Fleming seedling.

*Origin.*—A selected seedling from stated cross.

*Type of plant.*—Hardy, herbaceous perennial with some tropical genetics.

*Classification.*—Variety of TROPICAL-HARDY™ *Hibiscus* plant.

*Propagation.*—Relatively easy to propagate by means of tissue culture or cuttings; holds its distinguishing characteristics through successive cuttings and propagations through cuttings and division.

*Size.*—About 3 feet tall and about 3 ft. wide by the second year.

*Form.*—Symmetrical annual growth from perennial roots.

*Habit.*—Upright and uniformly branched.

*Growth.*—Vigorous; small and very compact. Full growth (3 ft.) in 2 years.

*Hardiness.*—Hardy to at least −30 degrees Fahrenheit.

General health: Plant is very disease resistant against rot, aphids, spider mites, scale, white fly, etc.; sturdy through excessive drought, rain, or wind.

Propagation: Relatively easy and fast rooting in approximately 2 weeks.

Foliage:

1. *Arrangement.*—Alternate.
2. *Shape.*—Juvenile: Variable, 3-lobed leaf. Rounded base shape. Mature: Refined, "maple-like", 3–5 lobed leaf with entire to extremely mildly serrate margins and acute apices; rounded base.
3. *Size.*—Mature leaf (petiole base to apex): Length is about 4 inches or 11 cm, width is about 3½ inches or 8½ cm.
4. *Color.*—Young leaves (upper side): L-5, PLATE 23, page 69. Mature leaves: (upper side): J-2, PLATE 24, page 71. Veins: L-3, PLATE 23, page 69. Coloration of the lower leaf surface: L-5, PLATE 23, page 69.
5. *Surface texture.*—Smooth with Medium to High sheen.
6. *Petiole length.*—About 1¼ inches or 3½ cm; Diameter: 3 mm.
7. *Petiole color.*—Green to K-1, PLATE 46, page 115.

Stems: The stems are stout at the base, becoming more slender toward the apices; coloration is consistent with the petiole. Coloration is consistent with the petiole (1E, page 71, PLATE 24). Surface texture is semi-smooth. Typical and observed stem length is approximately 1 inch. Stem diameter is between ½ inch and 1¼ inches. Internode length is approximately 1 inch to 1½ inches.

THE FLOWER

Blooming period: Profuse from July until frost.

Flower diameter: Medium to large; about 6½ inches (16 cm).

Borne: Singly in leaf axils, from midpoint of stems upward.

Bloom duration: Individual bloom lasts at least one full day, sometimes 2.

Form: Campanulate; petals are also very overlapping with a conical shape and recurved petal edges.

Bud:

1. *Length.*—About 2 inches (or 5½ cm) on day before opening. Diameter is 1½ to 2 inches.
2. *Color.*—J-5, PLATE 4, page 31.
3. *Surface texture.*—Semi-glabrous.
4. *Duration.*—One to two weeks.

Corolla: Having 5 petals.

1. *Petal character and dimensions.*—Campanulate and very overlapping. Length is about 4¼ inches or 11 cm. Width is about 4¼ inches or 11 cm.
2. *Coloration.*—Pale pink petals. (a) Pale pink petals: F-2, p. 29, PLATE 3. Coloration of lower petal surface: Slightly lighter than F-2, pg. 29, PLATE 3. (b) Veination in petals: I-3, pg. 29, PLATE 3. (c) Eye Zone: L-5, pg. 29, PLATE 3.
3. *Texture.*—Smooth.
4. *Substance.*—Thick.
5. *Shape.*—Campanulate and very overlapping; tubular with recurved petal edges.

Reproductive organs:

1. *Staminal column.*—Stamen along basal two-thirds. Stamen length: About 2¼ inches (or 5.5 cm). Stamen color: B-1, pg. 29, PLATE 2. Pollen color: E-2, pg 31, PLATE 4.
2. *Style.*—Terminates upper one-third of staminal coumn. Stigmatic lobe color: A-6, pg. 45, PLATE 11.

Calyx: Connate at the base; about 1¾ inches (or 4.5 cm) in length. Color: 6-2, page 23, Plate 23.

Stipules: None.

Epicalyx: Whorl of bracts.

1. *Shape.*—10 to 12 slender, sword-shaped bractlets.
2. *Length.*—About 1 inches (or 2¼ cm).
3. *Color.*—L-5, pg 67, PLATE 22.

Penduncle:

1. *Typical.*—About 2 inches (6 cm). Observed length: 2½ inches (6.5 cm).
2. *Strength.*—Stiff and sturdy.
3. *Color.*—6-2, page 23, Plate 23.

Seeds:

1. *Diameter.*—1 cm.
2. *Shape.*—Round.
3. *Color.*—Brown: 8A, page 23, Plate 15.

Roots of plant: Consistent with that of *Hibiscus moscheutos;* white, 1–3 inch wide fibrous root system with middle "tap" root that can descend 10 ft.

GENERAL OBSERVATIONS

This plant, as hybridized TROPICAL-HARDY™ *Hibiscus,* is valuable to the landscape market for its improvements in tropical aspect, pink tubular flowers with recurved edges, shiny and very refined, Maple-like green foliage on a much more compact, pyramidal plant that will grow nicely in patio pots, its all-around vigor, good breaking action, and adaptation to extreme environments, including the ability to consistently survive winter temperatures of at least −30 degrees Fahrenheit.

What is claimed:

1. A new and distinct cultivar of TROPICAL-HARDY™ *Hibiscus* plant, as herein shown and described, characterized by its tropical aspect, extremely compact, pyramidal nature, its shiny and very refined green, Maple-like foliage, its pale pink tubular flowers with recurved petal edges, its vigor, and its hardiness.

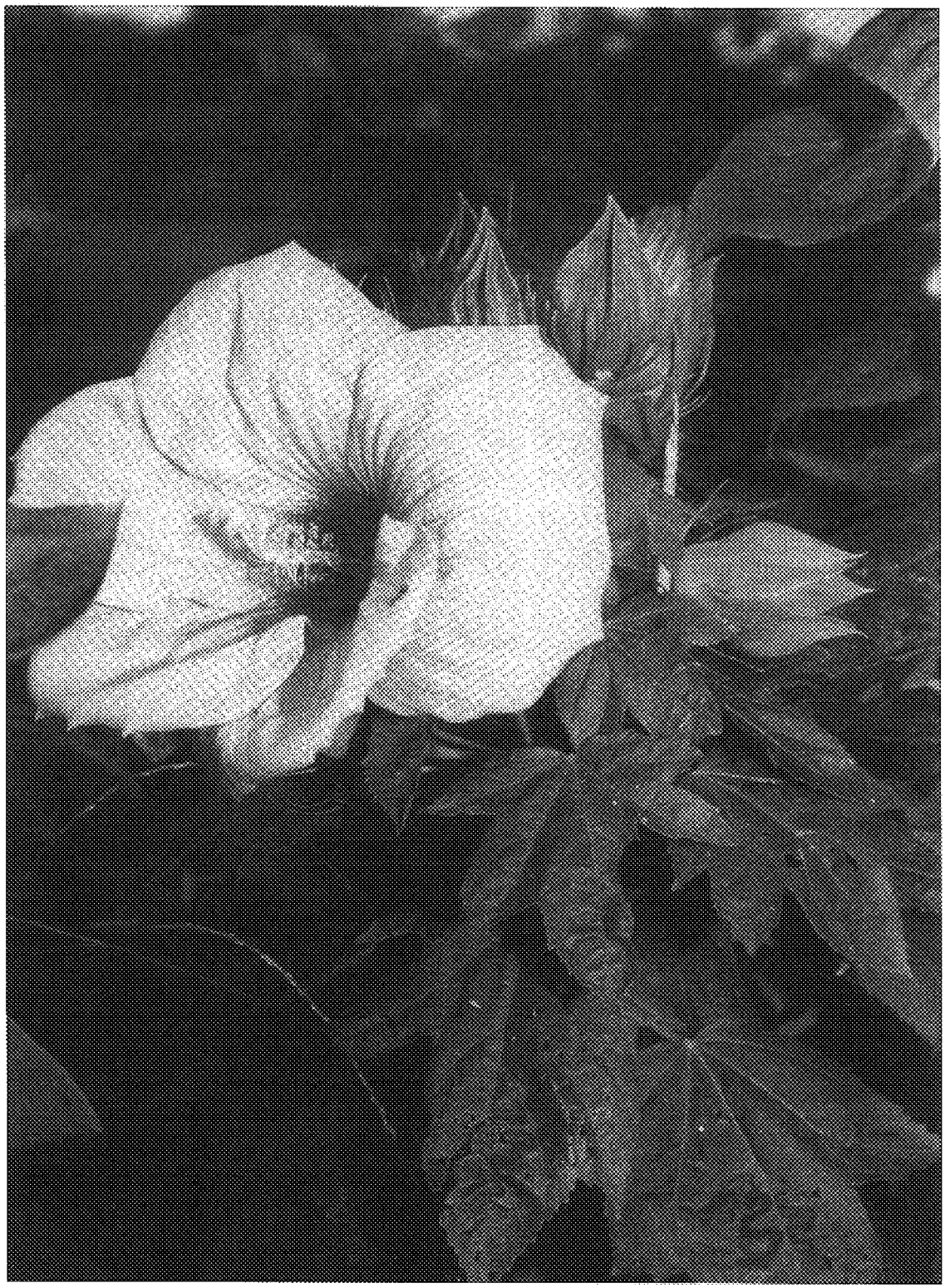

* * * * *